(12) United States Patent
Brooker

(10) Patent No.: US 6,468,736 B2
(45) Date of Patent: Oct. 22, 2002

(54) HIGH EFFICIENCY CELL ANALYSIS SYSTEM AND HIGH THROUGHPUT DRUG SCREENING SYSTEM

(75) Inventor: Gary Brooker, Rockville, MD (US)

(73) Assignee: Atto Instruments, LLC., Rockville, MD (US)

( * ) Notice: Subject to any disclaimer, the term of this patent is extended or adjusted under 35 U.S.C. 154(b) by 0 days.

(21) Appl. No.: 09/886,102

(22) Filed: Jun. 22, 2001

(65) Prior Publication Data

US 2002/0031789 A1 Mar. 14, 2002

Related U.S. Application Data

(60) Provisional application No. 60/213,179, filed on Jun. 22, 2000.

(51) Int. Cl.$^7$ ................................................. C12Q 1/00
(52) U.S. Cl. .................... 435/4; 435/30; 435/286.4; 435/287.3; 435/288.4; 435/288.7; 356/904
(58) Field of Search ............................... 422/62, 82.05, 422/4, 7.1; 435/30, 286.2, 286.4, 287.3, 288.7, 288.4; 356/904

(56) References Cited

U.S. PATENT DOCUMENTS

| | | | |
|---|---|---|---|
| 5,804,436 A | 9/1998 | Okun et al. ............... | 435/286.1 |
| 5,981,733 A | 11/1999 | Gamble et al. ............ | 536/25.3 |
| 6,001,309 A | * 12/1999 | Gamble et al. ............. | 422/100 |
| 6,136,269 A | 10/2000 | Winkler et al. ............... | 422/61 |
| 6,235,473 B1 | 5/2001 | Friedman et al. .............. | 435/6 |

\* cited by examiner

Primary Examiner—David A. Redding
(74) Attorney, Agent, or Firm—Oblon, Spivak, McClelland, Maier & Neustadt, P.C.

(57) ABSTRACT

A system which can analyze compounds with high efficiency, such as in a high throughput drug screening system. The high throughput drug screening system which can test the action of a drug candidate upon a group of cells in a monolayer. A microspace corresponding to a microscopic field area, for example on the order of 100–200 microns in diameter, is isolated from the other cells on the monolayer by creating a seal between a drug delivery perfusion unit and the cells to create the microspace for analysis. A drug candidate is then provided into the isolated microspace. The interaction between the drug candidate and the cells in the isolated microspace can then be evaluated. With the high throughput drug screening system the vast majority of cells on a monolayer can be used for drug testing. The high throughput drug system also makes it more readily available to use primary cells in addition to immortal cells as the cell layer.

23 Claims, 12 Drawing Sheets

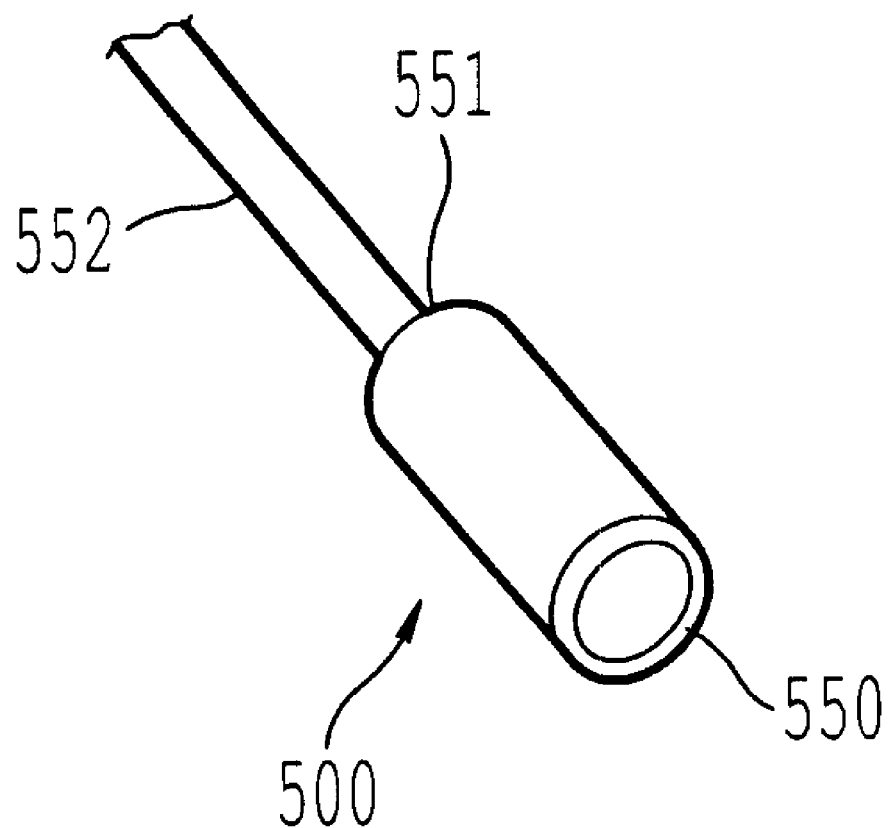

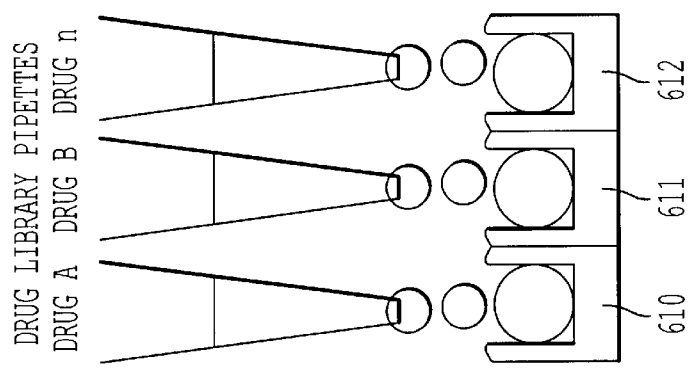
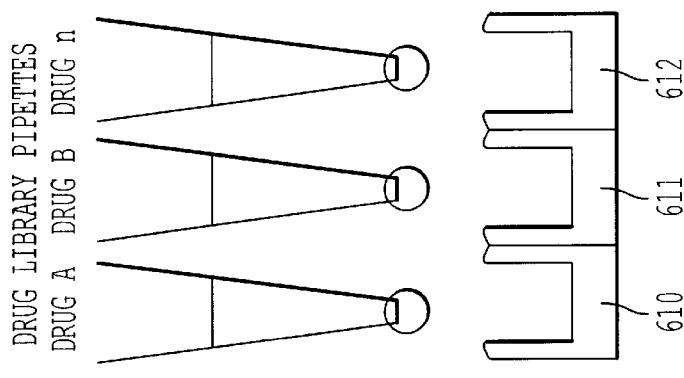
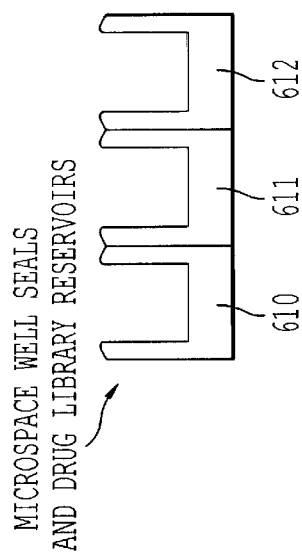

HIGH EFFICIENCY CELL ANALYSIS SYSTEM AND HIGH THROUGHPUT DRUG SCREENING SYSTEM

BACKGROUND OF THE INVENTION

1. Field of the Invention

The present invention is directed to a system which dramatically increases the speed and efficiency by which substances can be tested for their effects upon a myriad of biochemical processes, for example in living cells. The system can be applied to many fields including application in high throughput drug screening. When applied to the field of high throughput drug screening the system only requires a fraction of the cells currently needed for such tests, enables microminiturization of the process, and reduces the cost of drug screening by reducing the amount of reagents, cells, and disposable materials utilized in the screening process.

2. Discussion of the Background

Scientific research in general, and medical research as a specific example, often requires the evaluation of certain compositions relative to other compositions, plant cells, animal cells, etc. A common example of such research would be in the discovery and development of new drugs.

The discovery and development of a new drug occurs via two main stages. An initial discovery stage aims to the identification and optimization of chemical lead structures among the numerous compounds synthesized to interact with a molecular target putatively involved in the pathophysiology of a human disease. A development stage then follows that assesses the pharmacokinetics, safety and efficacy properties of those drugs found to be potential candidate in humans. Recent advances in drug discovery include the synergistic development of two new technologies in biomedical research known as Combinatorial Chemistry (CC) and High Throughput Screening (HTS). CC, via computer-aided drug design and automated organic synthesis, allows thousands of compounds (a library) of systematic variants of a parent chemical structure to be produced in parallel. Pharmaceutical researchers can now create in a relatively short time millions of new compounds designed to target a specific cellular substrate such as receptors, enzymes, structural proteins and DNA, thus increasing the need for rapid and broadly applicable methods to screen these compounds. While it is important to screen compounds for the targets they were designed for, it is also important to be able to screen compounds for their unintended targets to anticipate potential side effects of selected candidate drugs and to find new uses for these substances if the side effect turns out to be a desired property. The development of HTS has been making it feasible, through automation and miniaturization techniques, to screen upwards to millions of drug candidates a year with robotic workstations running continuously 24 hours a day, 7 days a week. Billions of animal cells expressing the molecular target against which a library is made are grown in 96, 384, or 1536 micro-well plates and, via automated drug and liquid delivery and computerized read-out devices, are tested for a biological response to the drugs.

In conventional HTS systems, animal cells are placed in each of the individual wells of the micro-well plates and are subject to many different processes to test for a response to applied drug candidates. However, an extremely large number of novel drug candidates can now be made available by CC. The conventional approach in HTS systems has been to increase the number of individual wells in the micro-well plates to increase the number of drug candidates that can be screened at one time.

The Scintillation Proximity Assay by Amersham, as disclosed in U.S. Pat. No. 4,271,139 and U.S. Pat. No. 4,382,074 as examples, is a one-step radioisotope-based assay that can be easily automated for HTS. However, the advantages of this sensitive and simple technique are challenged by increasing constrains on the use as well as the cost of disposal of radioactive materials. Thus, new nonradioisotope based screening alternatives have been sought. The development of fluorescent probes able to penetrate living cells, or be biochemically synthesized by cells, such as with chimeric constructs of green fluorescent proteins (GFP), and target protein receptors and enzymes in combination with improved optical instrumentation and means of delivering light and detecting signals has made fluorescence based technique the preferred alternative for many research applications. Fluorimetric Imaging Plate Reader (FLIPR) is a recently developed technique which permits kinetic measurements of intracellular fluorescence on cells labeled with an indicator whose fluorescence properties change upon binding to a cellular substrate targeted by a given drug. FLIPR allows for simultaneous and real time measurements of 96 (and recently 384) samples every second and finds an ideal application in HTS for candidate drugs targeting cell membrane receptors or channels whose activation leads to intracellular ion fluxes in a matter of seconds as in the case of the internal release or influx of calcium ions. In the pharmaceutical industry, HTS is currently performed on commercially available cell lines established from a variety of embryonic and adult animal tissues both normal and pathological. To create cell lines, cells are made immortal via exposure to defined agents such as viruses or chemicals thus acquiring the ability to continuously grow and divide in culture. However, it is generally recognized that, as a result of the immortalization procedure, changes in the expression of certain genes can randomly occur leading to a cell phenotype which might deviate from that of the parental tissue. For example, immortalized liver cells might have lost the ability to express a certain receptor, or to express it in the correct form or cellular compartment as the parental liver cells. Consequently, upon establishment, cell lines are tested for the expression of specific markers, receptors, enzymes, etc. and categorized accordingly.

In contrast to immortal cell lines, primary cell cultures derive from cells freshly isolated from a given organ or tissue. No viral or chemical intervention are used to pressure the cell division cycle and, thus, the cells will survive in vitro for only a short period of time, generally 10–15 days, and need to be re-established quite frequently during a research project. Primary cells are obtainable from a variety of animal models as well as human tissues surgically removed mainly for pathological reasons. Because of their short life span, primary cells maintain the biological stigmata of the original tissue virtually unchanged and, thus, are the research model considered closest to the in vivo environment. Therefore, drug screening on primary cells is highly desirable because it both decreases the chances to miss a valuable lead and increases the physiological relevance of the data collected. However, the dependence of conventional HTS on a tremendously high volume of biological substrate—billions of cells grown and processed in 96-, 384-, or 1536-micro-well plates—has prevented the application of widespread drug screening to primary cells because they are only available in limited quantities. Thus, cell lines exhibiting the biological target against which a drug library has been made are the unique and invaluable source of biological substrate fitting the needs of HTS currently available in drug discovery.

In many of the currently available HTS methodologies—e.g. fluorescence imaging based—the vast majority of cells grown are wasted because, among all the cells present in a given well and exposed to a drug candidate, only those occupying a microscopic field are ultimately monitored for their response. Along with the cells, precious chemical compounds and expensive reagents and supplies are dissipated making the process wasteful and time-consuming, thus reducing the overall afforded by HTS. As discussed above, conventional HTS systems provide individual cells in individual wells of micro-well plates. FIG. 1(a) shows a standard 96-well micro-well plate 100 including 96 individual wells 110, and an individual well 110 is shown in FIG. 1(b). Each micro-well 110 has a diameter D, which in the example of the standard 96 well plate 100 is 6 mm.

Currently available HTS systems perform the screening on the micro-well plates with a process such as shown for example in FIG. 2. In an example of utilizing the 96 well format in a first step S20, as shown in FIG. 2, cells are plated under aseptic sterile conditions and grown into each of the 96 wells. During the growth phase under aseptic sterile conditions, removal of growth media must be made from each well and new media repipetted into each well under aseptic sterile conditions. Once the cells are grown, then the wells are treated in step S25, which may include, as an example, loading the cells with a fluorescent dye, which again requires removal of media from each well, addition of the dye, incubation for a period of time, etc. Then, in step S30 rinsing of the cells is executed for, as an example, removal of dye from each well. Finally drug candidates are added to each well and the cell response is measured in step S35 and the plates are then discarded in step S40.

The conventional HTS process shown in FIG. 2 suffers from the following drawbacks. First, in that process cells are grown into the entire area of each of the 96 wells, which means that that entire area of each of the 96 wells must be loaded with the fluorescent dye, the drug candidate, and any other reagents needed. Further, in the conventional HTS process of FIG. 2 as there are only 96 wells only 96 drug candidates can be evaluated at a single time. Although that may be a significant number of drug candidates, the HTS system relies on evaluating tens of thousands of drug candidates to determine whether the drug candidates provide a desired reaction with the cells. Therefore, evaluating only 96 drug candidates at one time is very time consuming evaluation process.

SUMMARY OF THE INVENTION

Accordingly, one object of the present invention is to provide a novel analysis system for analyzing a sample in a highly efficient manner.

A more specific object of the present invention is to provide a novel cost effective HTS system which greatly improves the efficiency, throughput, and physiological relevance of HTS drug screening.

A further object of the present invention is to provide a novel HTS system which dramatically reduces the number of cells used for each measurement and which also reduces the amount of reagents and disposable materials used in the HTS process.

A further object of the present invention is to provide a novel HTS system which can be effectively used with primary cells in addition to immortal cells.

The mainstream of the pharmaceutical industry is moving to solve HTS throughput problems by developing multiwell plates with more, and thus smaller, individual wells per plate. The current trend in the HTS industry is to move from 96 well plates 100 such as shown in FIG. 1 to 1536 well plates, a 16 fold increase in the number of wells per plate and a 16 fold decrease in the size of each individual well. Coincident with this is increased complexity: 1) of growing cells in the smaller wells, 2) in optics, 3) in fluid handling, and 4) of the mechanics involved with the process-all under aseptic sterile conditions. These drawbacks are in addition to the expenditure of untold hundreds of millions of dollars to achieve probably less than an order of magnitude increase in speed without other significant technological advantages which would increase the information content of the screening process.

The inventor of the present invention, however, has taken a contrary approach to that taken by the mainstream in the pharmaceutical industry. The inventor of the present invention has specifically not taken an approach to reduce the size of a micro-well, but has taken an opposite approach which can maintain the existing well structures, and in fact with the novel HTS system of the present invention cells can even be grown on monolayers without any predetermined well structure.

To achieve the above and other objects, the novel HTS system of the present invention tests the action of a drug candidate upon a group of cells in a monolayer such that a microscopic field area of 100–200 microns in diameter is isolated from other cells on the monolayer by creating a seal between a drug delivery perfusion unit and the cells to create a microspace for analysis. The novel HTS system of the present invention can provide improved efficiency over current HTS methods since the vast majority of the cells on a monolayer can be used for drug testing rather than wasting most of the cells and reagents, as is currently the case with HTS technology based upon cells grown in multi-well plates.

Further, the novel HTS system of the present invention can provide improved efficiency over current HTS systems since the HTS system of the present invention can more readily be used with primary cells as a first screen rather than requiring immortal cells for such an initial screening of compounds. Primary cells have exactly the same biological characteristics as do any cell in the body, because in fact that is exactly what they are, cells isolated from an animal and kept in cell culture for a short time. Because the number of primary cells available is somewhat limited, the efficient use of cells by the present invention makes it feasible to use primary cells for HTS with the present invention.

BRIEF DESCRIPTION OF THE DRAWINGS

A more complete appreciation of the present invention, and many of the attendant advantages thereof, will be readily obtained as the same becomes better understood by reference to the following detailed description when considered in connection with the accompanying drawings, wherein:

FIG. 5(c) shows a probe which can be utilized to implement the HTS system of the present invention; and FIGS. 6(a) and 5(b) show an overview of a further embodiment of the HTS system of the present invention.

DESCRIPTION OF THE PREFERRED EMBODIMENTS

Figure 1A:
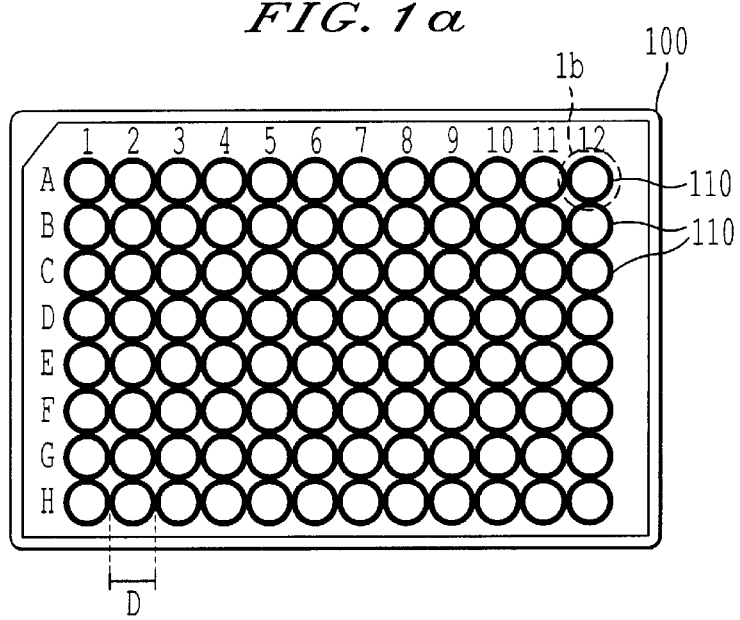
FIGS. 1(a) and 1(b) show a standard 96 well multi-well plate used in conventional HTS systems.

Referring now to the drawings, wherein like reference numerals designate identical or corresponding parts throughout the several views, the present invention will now be described.

The inventor of the present invention has recognized that in a conventional HTS system the area within each individual micro-well that is actually analyzed is quite small, and is typically on the order of only 100 microns. That is, with the conventional HTS system the imaging point of a microscope placed underneath the micro-well plates has an evaluation area of only approximately 100 microns. Therefore, the vast majority of area within each individual micro-well is not even evaluated and is essentially wasted.

The conventional HTS approach has thus been to make the area of each micro-well smaller and smaller and to utilize more micro-wells on each individual plate, and thereby 1,536 well plates are now being utilized. However, there is a limit as to how small each individual well can be, and thereby there is a limit as to how many different wells can be formed on a single multi-well plate. Specifically, as the individual micro-wells become smaller and smaller it becomes more difficult to grow cells in such micro-wells A myriad of problems exist when growing cells in such small wells, especially under aseptic sterile conditions. There are edge effects wherein cells do not evenly distribute or grow uniformly in the well, and there are, for example, problems of depositing uniform numbers of cells in each well. It also becomes more complicated to image the different individual micro-wells, supply fluid to the individual micro-wells, and to control the general mechanics of evaluating the interaction between the drug candidates and the cells in each of these smaller individual micro-wells.

Figure 1B:
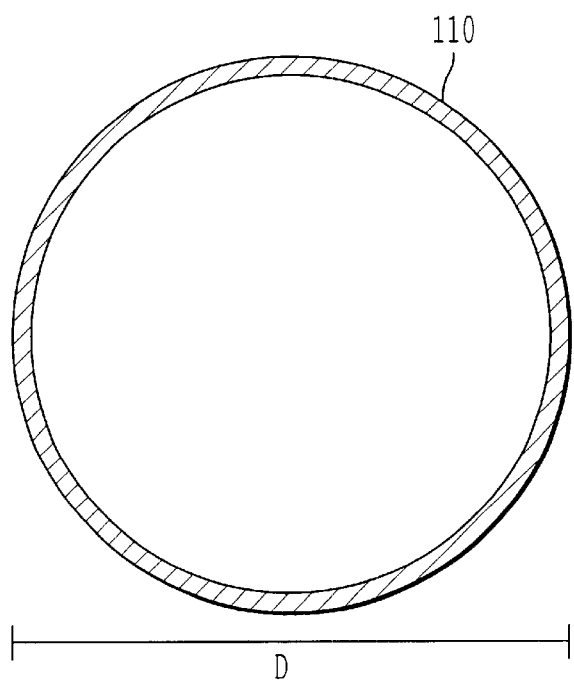
Figure 3A:
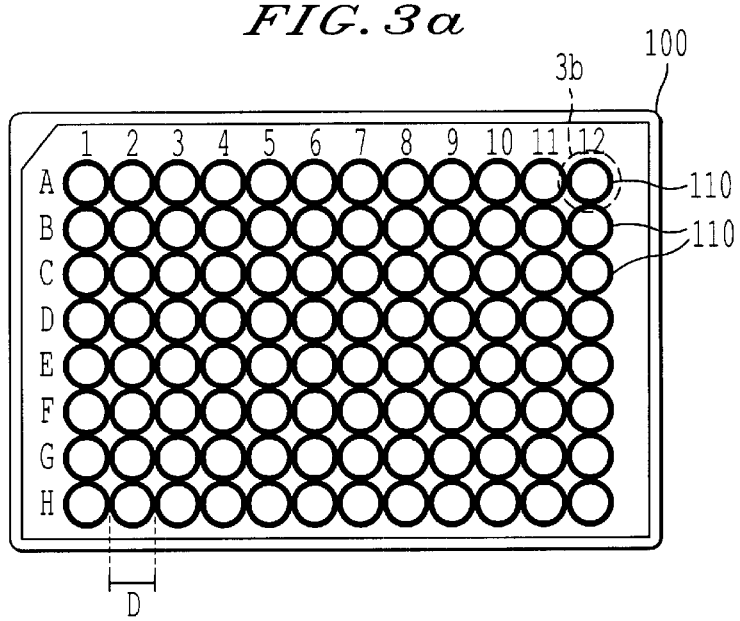
FIGS. 3(a)–3(c) show how many 100 micron microspaces can be generated in one individual well of a conventional 96 multi-well plate as a feature of the present invention.
Figure 3B:
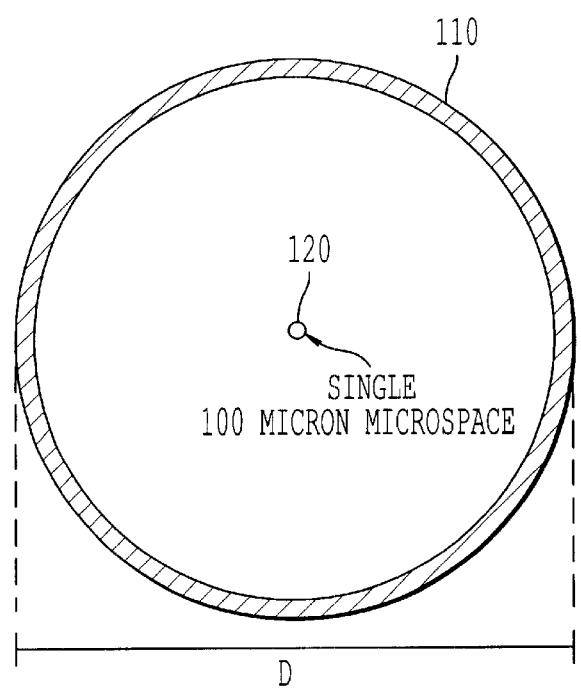
Figure 3C:
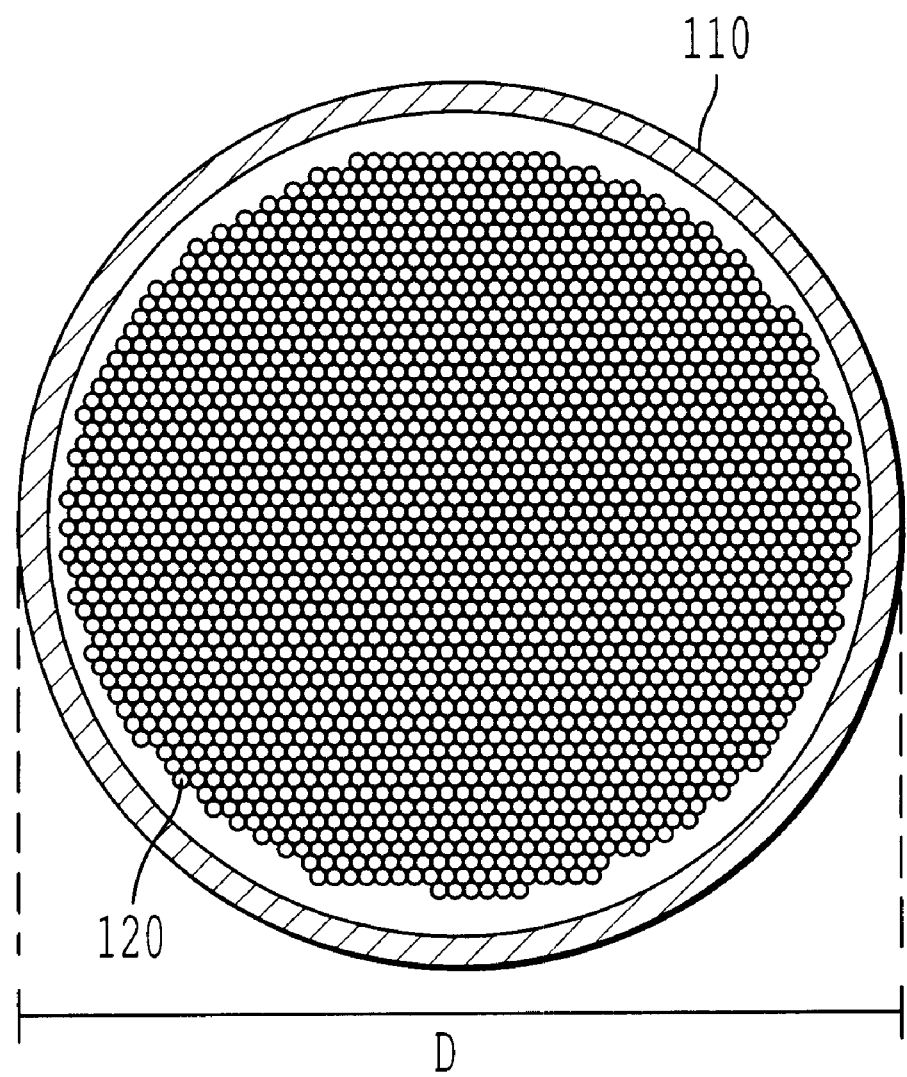
Figure 4A:
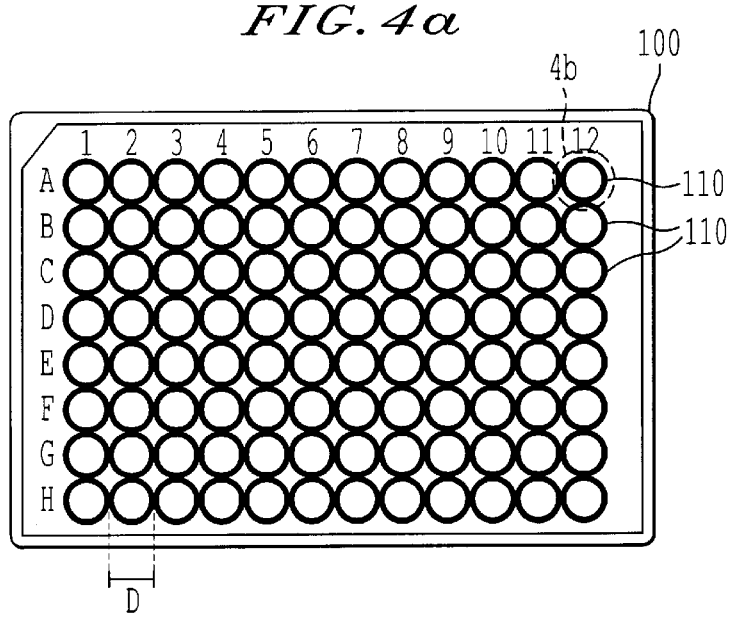
FIGS. 4(a)–4(c) show how many 200 micron microspaces can be generated in one individual well of a conventional 96 well multi-well plate as a feature of the present invention.
Figure 4B:
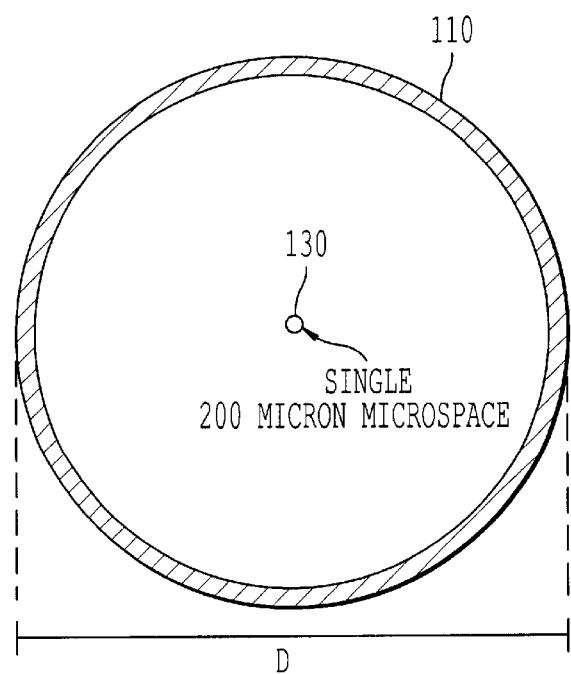

To graphically illustrate how much space in the standard micro-well plates is not being utilized in conventional HTS systems, attention is drawn to FIGS. 3 and 4. FIG. 3(a) shows a standard 96-well microplate 100 as in FIG. 1. FIG. 3(b) also shows the approximate space taken up by a single 100 micron point 120, which is typically the point imaged by the microscope placed underneath the multi-well plate, on an individual well 110 of the microplate 100. FIG. 3(c) shows how many individual 100 micron microspaces 120 can be fit into the standard 6 mm diameter well 110. As is evident from FIG. 3(b), the great majority of cells in each 6 mm diameter well 110 are essentially wasted, as is further quantified below.

Figure 4C:
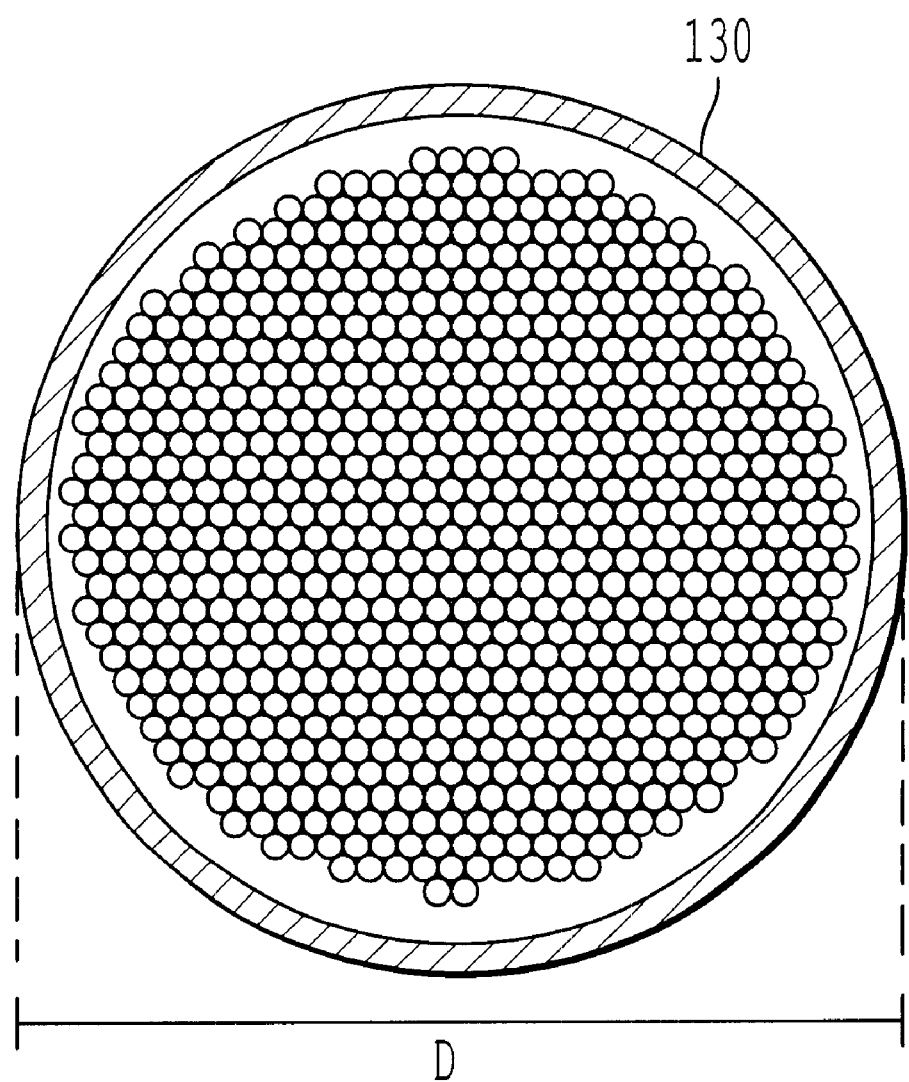

FIG. 4 shows a similar analysis for a single 200 micron microspace 130, and FIG. 4(c) shows how many individual single 200 micron microspaces 130 can be formed in a single 6 mm diameter well.

As seen in FIGS. 3 and 4, only a very small area of a single well 100 from a 96 well plate 100 is necessary to perform an analysis. If the 100 micron diameter microspace 120 is selected from a single well, there are about 2000 additional microspaces 120 in that same well, as shown in FIG. 3(c). Thus, if the 100 micron diameter microspaces are evaluated, then almost 200,000 different microspace regions are potentially possible for analysis with only the cells grown on one 96 well plate. Moreover, there may be on the order of 40 cells in the 100 micron microspace 120 in an example in which the well 110 has about 40 cells, which is a very adequate number of cells for HTS applications. As shown in FIG. 4, the 200 micron diameter microspace 130 is placed in the well 110. In that case there are about 700 microspaces of 200 micron diameter microspace 130 in one well 110 from a 96 well plate. In that case there would be more than 60,000 microspace assay areas available with the cells from one 96 well plate; and in this case one could measure the response in more than 100 individual cells per region, also in the example of the well 110 containing about 100 cells.

Figure 5A:
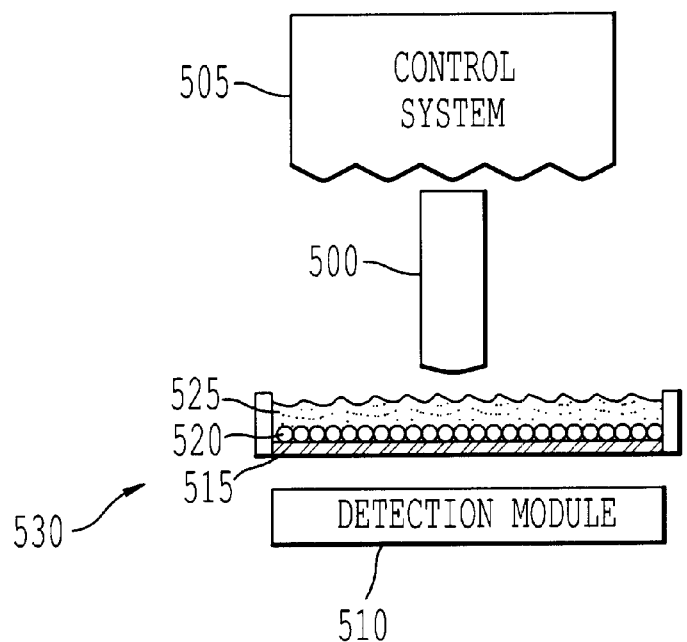
FIGS. 5(a) and 5(b) show an overview of one embodiment of the HTS system of the present invention.
Figure 5B:
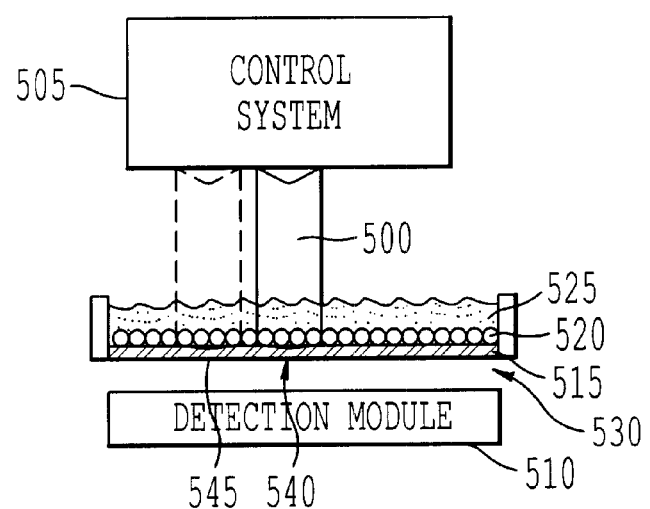

FIGS. 5(a)–5(c) show one specific implementation of the HTS system of the present invention.

Figure 2:
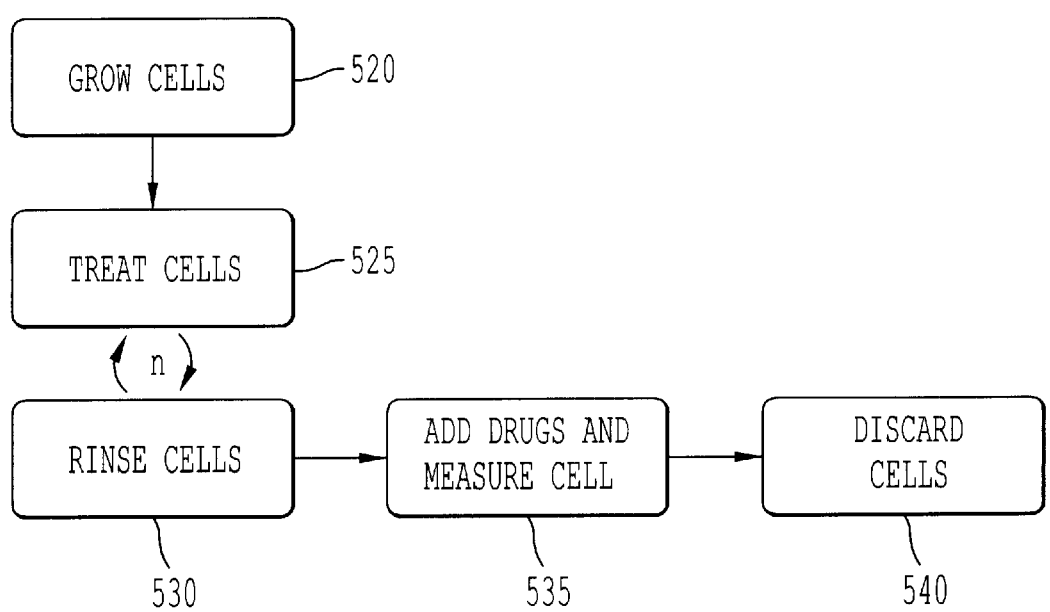
FIG. 2 outlines an operation in a conventional HTS system.

As shown in FIG. 5(a), in the HTS system of the present invention a cell container 530 contains a substrate 515, a layer or layers of cells (which for convenience we hereinafter refer to as the "monolayer") 520 formed above the substrate 515, and a solution, i.e., a buffer, 525 formed on top of the cell monolayer 520. The cell container 530 may be one individual well 110 of a 96 well plate 100 as shown for example in FIGS. 1–3. However, the cell container 530 is not limited to such a container and could be any standard laboratory cell plate of 2.5 cm or other diameter or any size or shape container which could support a layer of cells.

One significant feature of the HTS system of the present invention is that the area of the cell monolayer 520 which is evaluated is an area within the outer boundaries of the cell container 530, i.e. multiple evaluations can be executed with the cell container 530 that is within the area of one individual well 110 of a multi-well plate.

Placed below the cell container 530 is a detection module 510. The detection module 510 may be a microscopic imaging system with microscope objective and appropriate detection optics for viewing or documentation or detection of the cells or their fluorescence, luminescence. Positioned on the opposite side of the cell container 530 of the detection module 510 is a drug delivery perfusion device 500. The drug delivery perfusion device 500 performs an important role in the HTS system of the present invention. The drug delivery perfusion device 500 is an element which is pressed down into the cell monolayer 520 to isolate one specific microspace of the cell monolayer 520. Then, when the one specific microspace of the cell monolayer 520 is isolated the drug candidate is injected into the isolated microspace. Then, the detection module 510 can evaluate the interaction between the cell monolayer 520 and the drug candidate within the isolated microspace to determine whether a desired reaction takes place. The movement of the drug delivery perfusion device 500 is controlled by a control system 505.

FIG. 5(a) shows a state of the HTS system of the present invention when the drug delivery perfusion device 500 is not isolating a microspace. FIG. 5(b), on the other hand, shows a state of the HTS system of the present invention in which the drug delivery perfusion device 500 is pressed into the cell monolayer 520 so that the edges of the drug delivery perfusion device 500 isolate a region 540 of the cell monolayer 520, i.e., region 540 is a microspace isolated by the drug perfusion device 500. Then, in the HTS system of the present invention, as noted above, a drug candidate is injected into the microspace 540 and the detection module 510 evaluates whether the reaction between the drug candidate and the cell monolayer 520 generates a desired result.

Then, as also shown in FIG. 5(b) (by the dashed lines), the control system 505 picks up the drug delivery perfusion device 500 and moves the drug delivery perfusion device 500 over a predetermined distance to isolate a next microspace 545. Before this is done the drug candidate, perfusion solution, and cells are removed from the substrate 515. This can be accomplished by chemical removal of the cells with a solution of NaOH, dislocation of the cells with a solution of EDTA, or by other chemical or non-chemical means. If chemical solutions are used to remove the cells, then the chemical means is removed prior to removal of the perfusion device 500 so as not to contaminate the remaining cells on the substrate 515 within the cell container 530. Once the drug delivery perfusion device 500 is in position over the next microspace 545, a second drug candidate can then be injected into the microspace 545 through the drug delivery perfusion device 500 to again evaluate the interaction between that second drug candidate and the cell monolayer 520 within the next microspace 545. The process is then repeated for next microspaces within the next one individual well, and the process is then repeated for the other individual wells in the multi-well plate.

FIG. 5(c) shows a specific construction that the drug delivery perfusion device 500 can take as a probe. As shown in FIG. 5(c), the probe 500 includes an outer edge 550 and two lines 551 and 552 providing an input and output to the outer edge 550. The outer edge 550 is a portion which is placed down through the cell monolayer 520 to provide an isolation of the microspaces 540, 545 shown in FIG. 5(b). While the drug delivery perfusion device 500 shown here is used to create one microspace, multiple drug delivery perfusion devices 500 can be placed together so that large numbers of microspaces can be created at one time.

With such a structure and operation in the present invention, a single probe can be utilized to isolate different microspaces of a cell monolayer 520, and different drug candidates can be provided to the cell monolayer 520 for each respective microspace. The diameter of the outer portion 550 of the probe 500, i.e., the portion which provides the isolation of the microspace, may be on the order of 100 or 200 microns. With such structures in the present invention, hundreds to thousands of individual microspaces as shown in FIGS. 3(c) and 4(c) can be evaluated for a single well of a 96 well plate.

Figure 6A:
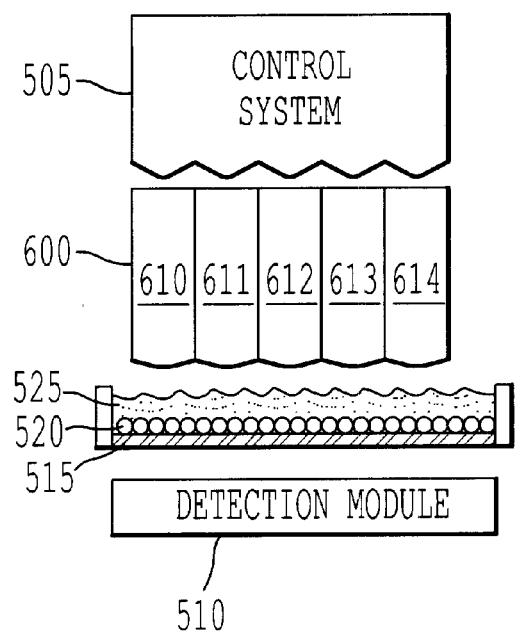
Figure 6B:
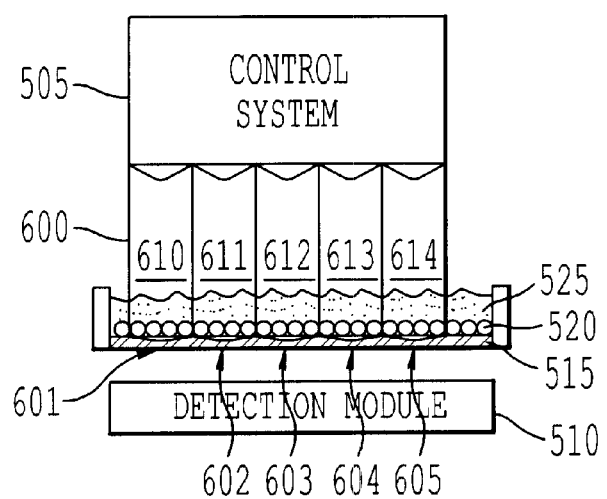

FIG. 6(a) and FIG. 6(b) show a second implementation of the HTS system of the present invention. The implementation shown in FIGS. 6(a) and 6(b) is similar to that as shown in FIGS. 5(a) and 5(b) except that a different probe element 600 is provided. The drug delivery perfusion device 600 in the embodiment of FIGS. 6(a) and 6(b) is an element which includes plural different portions 610–614. Further, each individual portion 610–614 isolates a respective microspace 601–605, as shown in FIG. 6(b).

In the specific implementation of FIGS. 6(a) and 6(b), each individual portion 610–614 may be equivalent to the probe 500 of FIG. 5(c).

However, an alternative form of the multiple drug delivery perfusion device 600 of FIGS. 6(a) and 6(b) can be as a matrix such as shown in FIGS. 7(a)–7(h).

In the implementation as shown in FIG. 7(a), the drug delivery perfusion device 600 includes the multiple elements 610–612 forming a matrix, and each matrix portion 610–612 is an individual reservoir which will be utilized to store a drug candidate or a different concentration in solution of the same drug candidate to be tested upon individual microspace areas of the monolayer cell 520 (not shown in FIG. 7, see FIG. 6). Each matrix portion 610–612 also makes a seal with the monolayer of cells 520 to thereby isolate small groups of the cells so that the individual drug candidates or solutions with different compositions may be specifically delivered to the isolated cells for testing. Each matrix portion 610–612 also can provide the ability to image or measure the cells to detect the effect of the drug candidates upon a parameter being measured.

One typical parameter which may be measured may be fluorescence if the cells on the monolayer 520 are labeled with a reporter fluorescent dye. Another parameter could be luminescence if the reporter substance emits luminescence upon change in the parameter being measured.

If each of the matrix portions 610–612 has a diameter of 200 $\mu$m, and thus if 500 of the individual matrix portions 610–612 are provided, 500 individual 200 $\mu$m areas of cells in the cell monolayer 520 may be evaluated. A matrix 600 including 500 individual matrix portions will fit in one 6 mm diameter well of a standard 96 well plate. In FIG. 7 only 3 matrix portions 610–612 of the 500 matrix portions are shown.

As shown in FIG. 7(a), the 3 matrix portions 610–612 are provided in an inverted position so that they are ready to receive a drug candidates solution Then, as shown in FIG. 7(b) different drug candidates, drugs A–N, are delivered by, for example pipettes, so that, as shown in FIG. 7(c), each individual matrix portion 610–612 includes a different drug candidate.

Figure 7F:
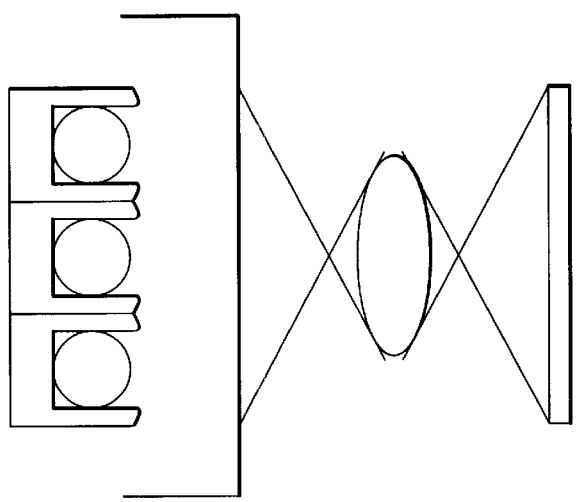
FIG. 7 shows a further probe which can be utilized to implement the HTS system of the present invention.
Figure 7E:
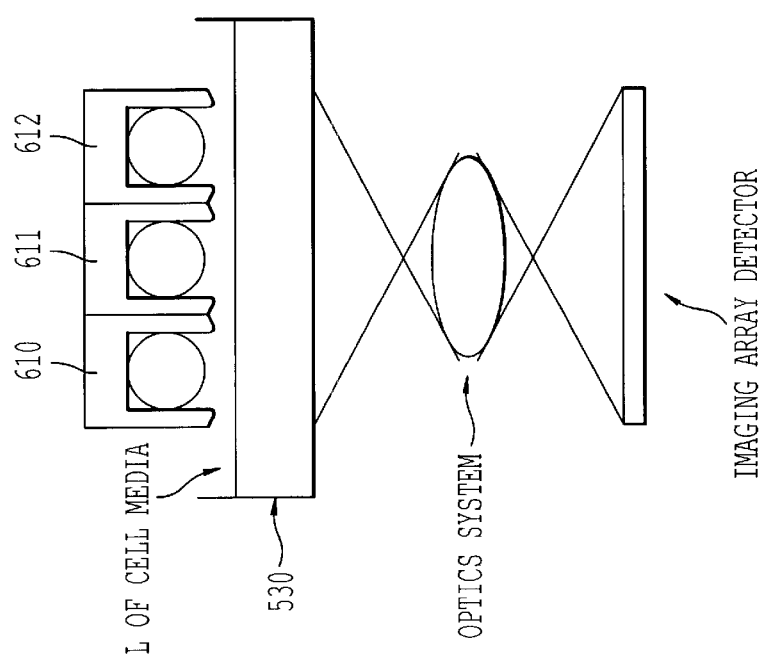
Figure 7D:
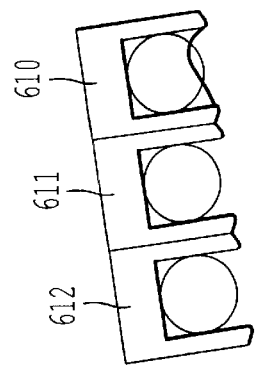

Then, the matrix is inverted as shown in FIG. 7(d). Because each individual matrix portion has a diameter of about 200 m, the liquids containing the drug candidates will remain in the matrix portions by capillary force. However since the quantities of drug being applied are so small the drug candidates can also be loaded with the matrix in the inverted position shown in FIG. 7(d). In this configuration the drug library pipets either fill the drug library candidates into the drug library reservoirs from the top or from the bottom. A variety of fluid transfer mechanisms are possible to accomplish this. They include capillary action or positive fluid pumping mechanisms.

As shown in FIG. 7(e), the matrix is then directed towards the cell container 530 which contains the cell monolayer 520. When a fluorescence measurement is being implemented a baseline fluorescence is measured for a specific time to determine fluorescence activity of the cell monolayer 520 before the drug candidates are added thereto, i.e., before the probe matrix contacts the cell monolayer 520. This fluorescence is either native to the cell monolayer due to the inherent fluorescence of substances in the cell, due to transfected genes which exhibit fluorescence, or is due to fluorescent or luminescent dyes applied to the cells.

Figure 7G:
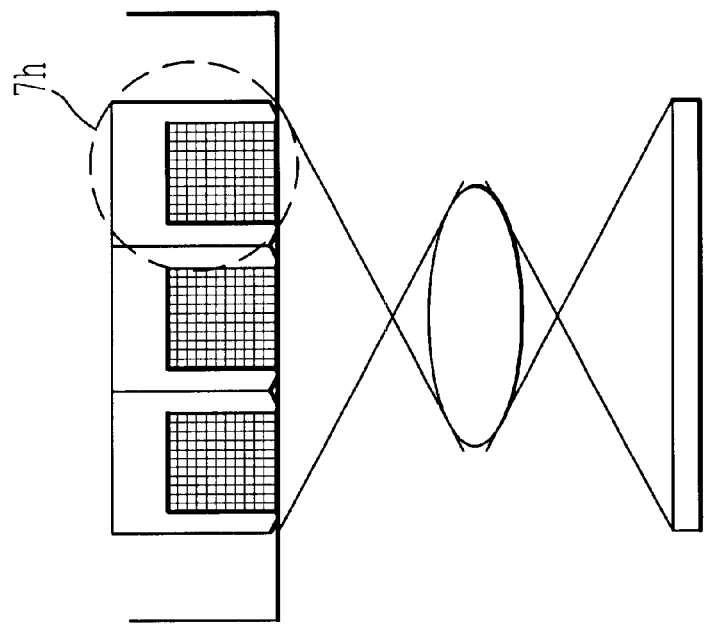
Figure 7H:
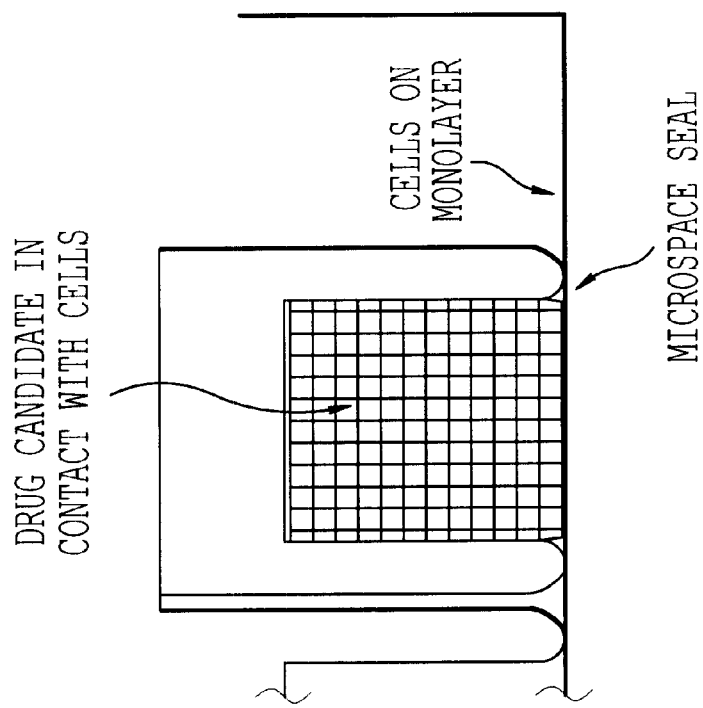

Then, as shown in FIG. 7(f) the media which covers the cells is aspirated and as shown in FIG. 7(g) the matrix is placed into the cell monolayer 520 to generate several individual microspaces At that time the drug candidates in the matrix portions 610–612 will interact with the cell monolayer within each of the individual microspaces. Then, an imaging of the change in fluorescence in each cell microspace caused by the reaction of each candidate drug within each cell microspace can be recorded and evaluated as a function of time the drug candidate is in contact with the cells.

In describing the above-noted specific limitations of the HTS system of the present invention it was noted that different drug candidates can be applied through the drug delivery perfusion devices. It should be clear that if desired the drug candidates need not all be different compounds, and drug candidates could take several forms such as different concentrations of the same compound, etc.

Thus, one feature of the present invention is to utilize the greater majority of cells grown on a simple monolayer for high throughput screening for greater speed, efficiency, and cost saving. If one were to practice the HTS system of the present invention in 96 well plates and monitor 100 micron diameter regions on each well, it would take almost 2000 plates to make the same number of determinations which are possible with the cells on one 96 well plate using the HTS system of the present invention. If one used 1536 well plates it still would require more than 100 plates. If one were monitoring 200 micron diameter regions from each well, one would need almost 700 96 well plates and more than 40 1536 well plates to effect the same number of determinations possible with the cells from just one 96 well plate.

As is evident from the above description, with the HTS system of the present invention, there is no specific requirement for the size of the substrate that the cells are grown upon nor is there any pattern requirement upon which the cells are grown. Thus, the HTS system of the present invention could be adapted to create a multitude of microspaces using current 96 well technology to get more throughput by adapting existing technology. In addition, new substrate sizes could be established for greater efficiency and improved and simplified mechanics or to address specific applications. For example, the surface area of all the wells in a 96 well plate is about equivalent to a 60 mm round disk or 50 mm square dish. In comparing the miniaturization possible to perform the same number of assays with the HTS system of the present invention versus the current microwell plates, the difference is dramatic. As an example, 60,000 assays using 1536 well density plates would require 40 plates and occupy a space of 435,000 $mm^2$, almost half a square meter. One dish of cells 50 mm square, which would fit in the palm of ones hand, would have an equivalent number of cells and only occupy an area of 2500 $mm^2$—a space saving and micro-miniaturization of more than 150 fold.

The HTS system of the present invention also provides other significant benefits, such as being particularly well adapted for applying drug candidates to primary cells rather than immortal cells because of the savings of cells wherein primary cells are not available in the quantities currently needed for HTS by the current technology before this invention. Further, the HTS system of the present invention provides significant benefits in being able to easily and readily apply any necessary chemical pre-processing to all the cells of the cell monolayer at the same time without the need to add the substances to each well.

Thus it would be much easier to grow cells on such a substrate and to simply add one solution to the disk, which is common to all the cells, for example when loading an indicator fluorescent dye. This would be in contrast to an assay in a 1536 well plate in which the indicator dye would have to be added to each of the 1536 wells in the plate.

The HTS system of the present invention can be configured to perform the most commonly used screening methods in standard HTS. Currently, the initial search for a valuable lead in drug discovery focuses on the downstream effect that drug candidates might exert on second messengers (molecules produced by the cell in response to external stimuli) which are turnkey factors in signal transduction.

The following is a specific example of how the HTS system of the present invention facilitates efficiency and throughput when implemented to screen for drugs designed to bind to receptors or channels known to stimulate increases in intracellular calcium ions. This is routinely performed by monitoring the release or the influx of calcium evoked by drugs and is commonly used to screen for drug candidates by conventional methods, mainly in immortal cells and with limited throughput. Calcium is probably one of the most ubiquitous second messengers involved in vital cellular responses including muscle and cardiac contraction, hormone secretion, and nervous transmission. Both the maintenance of physiological calcium levels within the cells and the biologically useful elevation of this second messenger are highly regulated processes bound to a myriad of cell process including cell growth and differentiation and ultimately whether a cell takes on a cancerous phenotype. Thus, a major effort is being put forth by pharmaceutical industry to develop new drugs which could 1) promote an intracellular increase of calcium when the cell itself is impaired in its ability to respond to calcium-elevating stimuli; 2) restore calcium homeostasis when the cell is unable to reduce sustained intracellular calcium increase upon stimulation; and 3) inhibit calcium increase when a calcium response is undesirable, such as in pathophysiological states.

A number of cell permeable, fluorescent probes sensitive to changes in intracellular calcium concentration have been developed, and are now commercially available (see Molecular Probes catalog, www.probes.com), to study the regulation of intracellular free-calcium levels $[Ca^{2+}]_i$ in living cells. Different dyes have distinct spectral characteristics which are affected by increased $[Ca^{2+}]_i$ in a specific fashion. The simplest model is a single excitation probe whose fluorescence emission increases when $[Ca^{2+}]_i$ increases (e.g. Fluo-3 and Fluo-4-488 nm excitation and 520 nm emission). Another model is a probe excitable by two different wavelengths while emitting at the same wavelength (e.g. Fura-2; 334–380 nm excitation and 510 nm emission). Upon binding $[Ca^{2+}]_i$, the emission coming from the two excitation wavelengths changes in a distinct way with one increasing and the other decreasing as a function of the ion concentration. The HTS system of the present invention will allow $[Ca^{2+}]_i$ fluorescent measurements currently performed on a multi-well plate on continuous monolayers of cells with the advantages of greater efficiency and cost efficacy.

The following example demonstrates the increased throughput and efficiency possible when measuring the calcium response of C6-2B glioma cells in culture after addition of a large battery of drug candidates using the principle of the present invention. In the present example, the effect upon the intracellular calcium response of 50,000 different substances added to cultured cells is to be determined. In this case we will contrast the workflow between the invention of the present application and currently available technology.

A. Testing in an Example of the Present Invention

The following discussion provides an example of a test which can be performed in the present invention. In the following discussion, assume that the invention of this application is used to monitor the action of 50,400 drug candidates upon calcium ion in C6-2B glioma cells. In that case, the following steps (1)–(6) are required.

(1) C6-2B cells are plated under sterile conditions at 10,000 cells/ml of DMEM media with 5% calf serum onto 1–96 well plastic plate with 0.5 ml/well. This requires a 48 ml (0.048 liter) stock solution of cells at a concentration of 10,000 cells/ml (480,000 cells) in DMEM supplemented with 2.4 ml (0.0024 liter) of calf serum. The 96 wells in the plate are filled with 0.5 ml of the plating solution. At a transfer time of 0.1 second/well it takes about 10 seconds to plate the cells.

(2) After three days in the incubator, under aseptic sterile conditions the media is withdrawn from all 96 wells and replaced with 48 ml of DMEM supplemented with 5% calf -serum. This operation takes 0.2 seconds/well and thus takes less than 20 seconds and utilizes another 48 ml of DMEM supplemented with 5% calf serum.

(3) Two days later the media is aspirated and 0.2 ml of a 5 micromolar solution of Fluo-4 AM in DMEM with 5% calf serum is added to each well. This requires 19.2 ml of DMEM, less than 20 seconds to pipet and 95 nanomoles of the fluorescent dye, Fluo-4 AM at a current (yr. 2000) market price of about $16.

(4) After a 30 minute incubation, the cells are washed once to remove fluo-4 from the media using another 48 ml of DMEM, which takes another 20 seconds and the 96 well plate is placed upon the microscope stage.

(5) Each of the 96 wells on this plate is then sequentially positioned on the microscope stage and a 500 microspace matrix drug delivery unit is prefilled with 500 individual drug solutions. Each microspace unit contains 1 to 5 microliters of drug candidate and the filling of each microspace unit can be performed in 0.2 second and thus each 500 unit matrix thus takes about two minutes to fill with 500 drug candidates. These 500 unit matrices can be filled off line in a separate station which picks up each drug candidate or drug solution, dilutes it and dispenses it into each unit in the microspace matrix drug deliver unit or can be filled on line while measuring functions are being performed. The area of each microspace created in the 500 unit matrix allows the imaging of about 100 cells. The optics and detector are designed to give the same pixel resolution as is seen with standard microscope imaging of cells with a digital camera. Thus in this case a larger pixel array in the detector is needed and the detector and optics are chosen to have sufficient resolution to image the majority of the 6 mm field of a single well of the 96 well plate which is occupied by the 500 unit microspace matrix drug delivery unit. Thus all 500 microspaces, each with 100 cells per unit, can be simultaneously monitored. Control fluorescence emission at 510–30 nm after excitation of the dye at 488 nm of each of the cells is monitored in a 200 micron diameter region of the well for 5 seconds. The media from the well is removed and the microspace matrix drug delivery unit is lowered to the cell substrate, creating 500 individual microspaces with either immediate drug delivery or delayed drug delivery depending on the configuration selected. Once the drug candidate makes contact with the cells, the fluorescence emission of each cell in each 200 micron region is then simultaneously monitored for another 10 seconds to determine if any change in fluorescence occurs. Increased fluorescence emission from any pixel indicates an increase in intracellular calcium concentration. The microspace matrix drug delivery unit is removed from the well and the next microspace matrix drug delivery unit is positioned over the next well of the 96 well plate. For each 500 drug matrix it takes less than three minutes and utilizes negligible reagent. If the drug library microspace units are filled offline, the process per well takes less than a minute. Thus to measure the effect of 50,000 different drugs on one cell type it would take between 1½ to 4½ hours.

(6) The one plate and less than 100 ml of media used for the experiment is discarded.

It is obvious that this magnitude experiment is not practically performed with current technology for a number of reasons. The cells cannot be left with dye loaded for such a long time. After a period of time the dye no longer can detect free intracellular calcium concentration, thus the incubation of the cells with the dye would have to be timed so that dye incubation could not be done in the parallel manner as shown above but would have to be added to cells in a sequential manner so that dye incubation and time before assay with drug candidate was the same for all drugs tested. Secondly, the cells being tested would have to also be plated in a timed manner into 525 plates (96 wells/plate×525 plates=about 50,000 wells) since cells in plate 1 vs. cells in plate 525 would have a difference in culture time of more than 200 hours. Thus the practical way to conduct an assay with 525 plates would be to split it into 10 separate assays with about 26 plates per assay. While this would still consume the 85 liters of media, require $8,000 of fluorescent reagent and orders of magnitude more drug candidate and still take at least 210 hours, the experiment could be done for cells which rapidly replicate but would take almost two weeks. In many cases, this type of large scale assay experiment would be impossible with some cell types, such as primary cells, which would be very important to use for screening and large scale assays. These cells, which behave as do living cells in the body, do not replicate rapidly or loose their phenotype while in culture. While the present example is shown using 96 well plates, the present invention provides miniaturization, and increases in speed and economy of almost three orders of magnitude over conventional techniques. While this example is contrasted with the current technology in 96 well plates, the current move to smaller well size and 1536 well plates creates many additional complexities, always requires pipetting steps under aseptic sterile conditions into each small well, even if a common reagent (such as the fluorescent indicator dye) is to be applied to all cells, and only increases the density of assays by 16 fold (1536/96) as compared to more than 500–1000 fold increase in density and efficiency shown in the current example of the present invention (1 plate versus 525 for the same number of assays).

B. Testing in the Conventional Technology of FIG. 2

The following discussion now provides an example of testing performed in the conventional technology. In the following discussion again assume the present technology is utilized to monitor the action of 50,400 drug candidates upon calcium ion in C6-2B glioma cells. In that case, the following steps (1)–(6) are required.

(1) C6-2B cells are plated under sterile conditions at 10,000 cells/ml of DMEM media with 5% calf serum onto 525-96 well plastic plates with 0.5 ml/well. This requires a 25 liter stock solution of cells at a concentration of 10,000 cells/ml (250,000,000 cells) in DMEM supplemented with 1.25 liters of calf serum. The 50,400 wells in the 525 plates are filled with 0.5 ml of the plating solution. At a transfer time of 0.1 second/well it takes 84 minutes to plate the cells.

(2) After three days in the incubator, under aseptic sterile conditions the media is withdrawn from all 50,000 plus wells and replaced with 25 liters of DMEM supplemented with 5% calf serum. This operation takes 0.2 seconds/well and thus takes a total of 168 minutes and another 25 liters of DMEM supplemented with 5% calf serum.

(3) Two days later the media is aspirated and 0.2 ml of a 5 micromolar solution of Fluo-4 AM in DMEM with 5% calf serum is added to each well. This requires 10 liters of DMEM, 168 minutes to pipet and 50 micromoles of the fluorescent dye, Fluo-4 AM at a current market price of about $8,000.

(4) After a 30 minute incubation, the cells are washed once to remove fluo-4 from the media using another 25 liters of DMEM, which takes about 168 minutes and each of the 525 plates is sequentially placed upon the microscope stage.

(5) Each of the 96 wells per plates is then sequentially positioned on the microscope stage and a field of about 100 cells is identified and control fluorescence emission at 510–530 nm after excitation of the dye at 488 nm of each of the cells is monitored in a 200 micron diameter region of the well for 5 seconds. Then the drug candidate is added in a volume of 50 microliters so that effective mixing will occur. The fluorescence emission of each cell in the 200 micron region is then monitored for another 10 seconds to determine if any change in fluorescence occurs. Usually a 20 to 63 power objective is used in conjunction with a detection camera such as a cooled CCD camera for imaging the cells. At a serial time of 15 seconds per well, it will take 210 hours to measure the response in all 50,000 wells (6) The 525 plates are discarded along with the 85 liters of media used for the experiment.

As is clear from comparing the two testing examples noted above, the testing operation in the present invention allows testing to be executed in a significantly shorter time than that available with current technology. Further, the testing operations executed in the present invention allow a significantly less amount of test drugs, reagents, dyes, etc. to be utilized. Since high throughput drug testing is dependent on the number of drug candidates which can be tested in a specific period of time, the present invention provides significant benefits over the existing technology.

The present invention as discussed above has also been described with specific reference to an example of high throughput drug screening. The present invention however is clearly not limited to just that environment, and the present invention can be applied to many different environments, a few examples of which are now further indicated below.

The concepts and techniques disclosed in the present invention could be used for a variety of purposes to analyze the responses of individual cells or sub regions of a substrate under a variety of conditions. Because the technique enables one to efficiently apply substances and analyze the response in such a small microscopic area, it becomes possible to perform some analyses, which were never possible before the present invention.

In the area of drug discovery, once the effect of test compounds has been observed and a substance is identified the effect of different doses of that substance upon specific biochemical responses is readily facilitated by the current invention. Rather than filling the drug library pipettes with different drugs, each pipette of the drug application matrix can be filled with a different concentration of the same drug such that a complete dose response relationship is simultaneously obtained for the respective response being measured. Another opportunity facilitated by the current invention is the ability to measure the antagonistic or potentiative effect of a substance upon a matrix of agents. Since the antagonist or potentiator can be readily added to all the cells, it is easy to do such, preincubate for a predetermined time, and then apply the test drugs in a matrix as described in the invention.

Because of the great efficiency of cell usage, drug screening and more detailed drug dose response relationships can not only be studied in immortal cultured cells which are readily abundant, but these studies are now possible on cells which are available in more limited quantities such as primary cells. Primary cells from human patients could be screened for specific responses to identify genetic mutations associated with certain disease states as a diagnostic technique. The phenotypic response of primary cells from a human or veterinary patient to a variety of substances could provide the basis for a diagnostic test. For example, just as bacteria are tested for sensitivity to antibiotics by antibiotic sensitivity testing, cancer cells from a patient could be tested for sensitivity to a battery of chemotherapeutic agents. Furthermore, the techniques claimed in this invention could even greatly facilitate antibiotic sensitivity testing wherein the battery of antibiotics are loaded into the drug library pipettes and the bacteria are grown on the substrate. In this mode the effect of the antibiotic on the bacteria would be monitored by a fluorescent dye which would monitor cells viability or the morphology or numbers of bacteria in each microspace after a certain time period could be observed with or without fluorescence.

Another application of the present invention is the ability to micro-miniaturize clinical chemistry. In this case the enzymatic substrate or enzymes are coated on the substrate and the drug pipettes are filled with patient samples and reagents. Once the microspaces are formed upon the substrate, the reactions can be monitored. This would dramatically improve throughput and reduce the amount of blood and body fluids which would be necessary for clinical analysis.

In another embodiment of this invention, the substrate could be coated with an antibody specific to a specific substance being measured. The unknown patient sample with labeled ligand (radioactive, fluorescent, enzyme) then forms the microspace and the analysis then is performed by monitoring the respective signal in each microspace in a competition assay such as RIA (radioimmunoassay) or FIA (fluorescence immunoassay). The amount of antibody, protein or enzyme could also be measured by monitoring the binding of these substances to the substrate containing their respective ligands or substrates.

Another opportunity afforded by the present invention is the ability to measure the response of a small tissue removed from a human or veterinary subject to a variety of agents. In this case a small surgical or punch biopsy from a tumor or organ could be analyzed for the cells response to a battery of agents as described above, except that the tissue would be directly analyzed and a multitude of individual microspaces formed on the tissue, each containing hundreds of cells which could be evaluated for physiologic and pharmacological responses.

In more advanced versions of this present invention, because of the basic concept of creating microspaces with specific drug delivery to each microspace, a special catheter could be developed which would contain the drug matrix and detection optics such that it could be inserted into a person to perform the analysis described in this invention in vivo. The catheter could be inserted, as are biopsy needles, but could perform the analysis in a non-destructive manner without removal of a tissue sample. One could envision using such a device inserted in veins and arteries to reach specific organs for analysis.

Especially when using the present invention to monitor tissues wherein the cells are not grown on a monolayer, the confocal or multi-photon observation technique, which would allow one to specifically detect different layers of cells, would be of considerable advantage. In this way multiple cell actions and interactions could be simultaneously monitored. This could be of advantage even when the current invention is used in cultured cells. In some cases the cells do not grow on single monolayers, but can tend to grow in multiple layers or different cell types can be intentionally grown in different layers for greater efficiency or to monitor cell-cell interactions.

Obviously, numerous additional modifications and variations of the present invention are possible in light of the above teachings. It is therefore to be understood that within the scope of the appended claims, the present invention may be practiced otherwise than as specifically described herein.

What is claimed is:

1. An analysis system for analyzing a sample, comprising:
a test substance delivery perfusion unit configured to isolate a microspace of the sample by isolating the microspace from portions of the sample outside of the microspace, and to deliver at least one test substance to the microspace.

2. An analysis system according to claim 1, further comprising a microscope to image the microspace.

3. An analysis system according to claim 1, wherein the sample is formed of primary cells.

4. An analysis system according to claim 1, wherein the sample is formed of immortal cells.

5. An analysis system according to claim 1, wherein said test substance perfusion unit includes a plurality of probe portions, each probe portion isolating a different microspace of the sample and delivering the at least one test substance to the respective isolated microspace.

6. An analysis process for performing analysis on a sample, comprising the steps of:
isolating a microspace of the sample by isolating the microspace from portions of the sample outside of the microspace;
delivering at least one test substance to the microspace; and
evaluating an interaction of the sample and the at least one test substance.

7. An analysis process according to claim 6, wherein the evaluating step images the microspace with a microscope.

8. An analysis process according to claim 6, wherein the sample is formed of primary cells.

9. An analysis process according to claim 6, wherein the sample is formed of immortal cells.

10. An analysis process to claim 6, wherein said isolating step includes a plurality of different microspaces portions of the sample and the delivering step delivers the at least one test substance to each of the respective isolated microspaces.

11. A high throughput drug screening system for performing high throughput drug screening on a sample, comprising:
a drug delivery perfusion unit configured to isolate a microspace of the sample by isolating the microspace from portions of the sample outside of the microspace, and to deliver a drug candidate compound to the microspace.

12. A high throughput drug screening system according to claim 11, further comprising a microscope to image the microspace.

13. A high throughput drug screening system according to claim 11, wherein the sample is formed of primary cells.

14. A high throughput drug screening system according to claim 11, wherein the sample is formed of immortal cells.

15. A high throughput drug screening system according to claim 11, wherein said drug delivery perfusion unit includes a plurality of probe portions, each probe portion isolating a different microspace of the sample and delivering a drug candidate compound to the respective isolated microspace.

16. A high throughput drug screening process for performing high throughput drug screening on a sample, comprising the steps of:
isolating a microspace of the sample by isolating the microspace from portions of the sample outside of the microspace;
delivering a drug candidate compound to the microspace; and
evaluating an interaction of the sample and the drug candidate compound.

17. A high throughput drug screening process according to claim 16, wherein the evaluating step images the microspace with a microscope.

18. A high throughput drug screening process according to claim 16, wherein the sample is formed of primary cells.

19. A high throughput drug screening process according to claim 16, wherein the sample is formed of immortal cells.

20. A high throughput drug screening system process to claim 16, wherein said isolating step includes a plurality of different microspaces portions of the sample and the delivering step delivers a drug candidate compound to each of the respective isolated microspaces.

21. An apparatus for evaluating an interaction of a sample with a candidate compound, comprising:
means for isolating a microspace of the sample by isolating the microspace from portions of the sample outside of the microspace, and for delivering a candidate compound to the microspace; and
means for evaluating interaction of the sample and the candidate compound.

22. An apparatus according to claim 11, wherein the sample is formed of primary cells.

23. An apparatus according to claim 21, wherein the sample is formed of immortal cells.

* * * * *